United States Patent
Lin et al.

(10) Patent No.: US 8,975,393 B2
(45) Date of Patent: Mar. 10, 2015

(54) SYNTHESIS OF 5-DEOXY-5'-FLUOROCYTIDINE COMPOUNDS

(71) Applicant: PharmaEssentia Corp., Taipei (TW)

(72) Inventors: Ko-Chung Lin, Lexington, MA (US); Chungsun Chien, Taoyuan County (TW)

(73) Assignee: PharmaEssentia Corp., Taipei (TW)

( * ) Notice: Subject to any disclaimer, the term of this patent is extended or adjusted under 35 U.S.C. 154(b) by 117 days.

(21) Appl. No.: 13/736,484

(22) Filed: Jan. 8, 2013

(65) Prior Publication Data

US 2013/0184451 A1  Jul. 18, 2013

Related U.S. Application Data

(60) Provisional application No. 61/586,415, filed on Jan. 13, 2012.

(51) Int. Cl.
*C07H 19/00* (2006.01)
*C07H 1/00* (2006.01)

(52) U.S. Cl.
CPC . *C07H 1/00* (2013.01); *C07H 19/00* (2013.01)
USPC .................................................. 536/28.51

(58) Field of Classification Search
CPC ................................ C07H 19/06; C07H 1/00
See application file for complete search history.

(56) References Cited

U.S. PATENT DOCUMENTS 5,453,497 A * 9/1995 Kamiya et al. ............. 536/28.52
5,472,949 A * 12/1995 Arasaki et al. .................. 514/49

* cited by examiner

*Primary Examiner* — Lawrence E Crane
(74) *Attorney, Agent, or Firm* — Cesari and McKenna, LLP

(57) ABSTRACT

This invention relates to a process of synthesizing a β-nucleoside compound of formula (I):

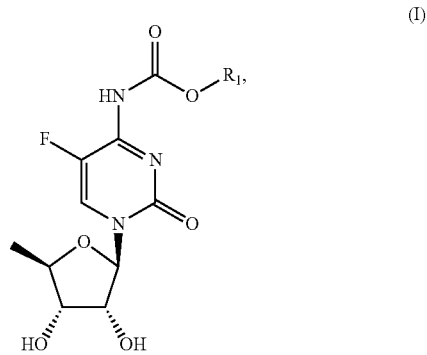

wherein $R_1$ is alkyl, aryl, cycloalkyl, heteroaryl, or heterocycloalkyl. The process includes reacting a compound of formula (II):

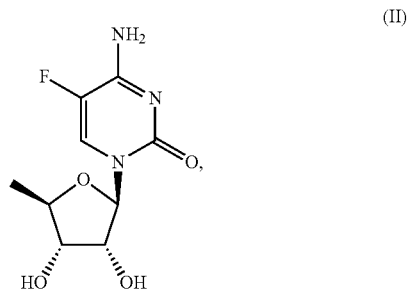

with a compound of formula (III):

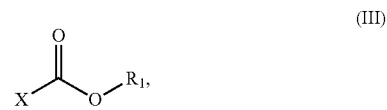

wherein $R_1$ is as defined above and X is chloride, bromide, iodide, methanesulfonate, triflate, p-toluenesulfonate, trifluoroacetate, 4-nitrophenoxy, or N-succinimidyloxy, in a solvent and in the presence of a base.

17 Claims, No Drawings

SYNTHESIS OF 5-DEOXY-5'-FLUOROCYTIDINE COMPOUNDS

CROSS-REFERENCE TO RELATED APPLICATIONS

This application claims the benefit of U.S. Provisional Application No. 61/586,415, filed on Jan. 13, 2012. The contents of the application are hereby incorporated by reference in its entirety.

BACKGROUND

5-Deoxy-5'-fluorocytidine compounds are therapeutically important agents. See U.S. Pat. No. 5,453,497. For example, N-pentyloxycarbonyl-5-deoxy-5'-fluorocytidine, also known as capecitabine, is a FDA-approved drug for treating colorectal cancer and breast cancer. It is enzymatically converted to 5-fluorouracil in tumor cells, where it inhibits DNA synthesis and slows tumor growth.

Synthesizing 5-deoxy-5'-fluorocytidine compounds is a challenging task given the existence of multiple chiral centers and active groups, i.e., hydroxyl groups. There is still a need to develop a more effective route for synthesizing 5-deoxy-5'-fluorocytidine compounds.

SUMMARY

One aspect of this invention relates to a process of synthesizing a β-nucleoside compound of formula (I):

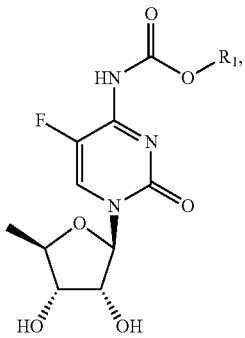

(I)

wherein $R_1$ is alkyl, alkenyl, aryl, cycloalkyl, heteroaryl, or heterocycloalkyl. The method includes reacting a compound of formula (II):

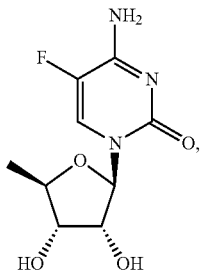

(II)

with a compound of formula (III):

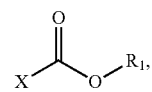

(III)

wherein $R_1$ is as defined above and X is chloride, bromide, iodide, methanesulfonate, triflate, p-toluenesulfonate, trifluoroacetate, 4-nitrophenoxy, or N-succinimidyloxy. This reaction can be carried out in a solvent containing a base at room temperature or an elevated temperature, e.g., of 50-100° C. (or 65-80° C.).

The solvent used in this reaction can be acetone, acetonitrile (ACN), dimethylformamide (DMF), ethyl acetate (EA), 1,2-dichloroethane (DCE), dimethylacetamide (DMAC), dimethylsulfoxide (DMSO), tetrahydrofuran (THF), isopropyl alcohol (IPA), nitromethane, or a mixture of one of the above solvents with water ($H_2O$), e.g., ACN/$H_2O$ or acetone/$H_2O$.

The base used in this reaction can be an organic base or an inorganic base. Examples include, but are not limited to, pyridine, imidazole, ammonia, monoalkylamine, dialkylamine, trialkylamine, sodium carbonate, potassium carbonate, and sodium bicarbonate.

Examples of the above-described method are such that: the compound of formula (III) is selected from those in which $R_1$ is alkyl (e.g., n-pentyl) and X is Cl, 4-nitrophenoxy, or N-succinimidyloxy; the base is pyridine or imidazole; and the solvent is DMF, DMSO, or DMAC.

The term "alkyl" refers to a straight or branched hydrocarbon, containing 1-6 carbon atoms. Examples of alkyl groups include, but are not limited to, methyl, ethyl, n-propyl, i-propyl, n-butyl, i-butyl, t-butyl, n-pentyl, and n-butyl.

The term "alkenyl" refers to a straight or branched hydrocarbon having one or more carbon-carbon double bonds. Examples of alkenyl groups include, but are not limited to, ethenyl, 1-butenyl, and 2-butenyl.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

The term "cycloalkyl" refers to a saturated or unsaturated, non-aromatic, cyclic hydrocarbon moiety. Examples of cycloalkyl groups include, but are not limited to, cyclopentyl, cyclohexyl, and cyclohexen-3-yl.

The term "heterocycloalkyl" refers to a saturated or unsaturated, non-aromatic, cyclic moiety having at least one ring heteroatom (e.g., N, O, or S). Examples of heterocycloalkyl groups include, but are not limited to, 4-tetrahydropyranyl and 4-pyranyl.

Alkyl, alkenyl, aryl, heteroaryl, cycloalkyl, and heterocycloalkyl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl, in which the alkyl, alkenyl, alkynyl, alkyloxy, aryl, heteroaryl, cyclyl, and heterocyclyl may be further substituted.

Other features, objects, and advantages of the invention will be apparent from the detailed description and the claims below.

DETAILED DESCRIPTION

This invention relates to an effective process for synthesizing 5-deoxy-5'-fluorocytidine derivatives, in particular, capecitabine, as well as novel intermediates produced in this process.

To practice this process, one first obtains the 5-deoxy-5'-fluorocytidine compound of formula (II). This compound can be prepared by deprotecting via hydrolyzing in acid or base 3,4-O-diacetyl-5-deoxy-5'-fluorocytidine, synthesis of which has been reported in U.S. Pat. No. 5,453,497. For example, 5-fluorocytosine is reacted with 5-deoxy-1,2,3-tri-O-acetyl-β-D-ribofuranoside in the presence of a Lewis acid to form 5-deoxy-2,3-O-diacetyl-5-fluorocytidine, which is then placed under an acidic or basic condition to allow the removal of the two acetyl protecting groups to obtain 5 deoxy-5'-fluorocytidine. See scheme 1 below:

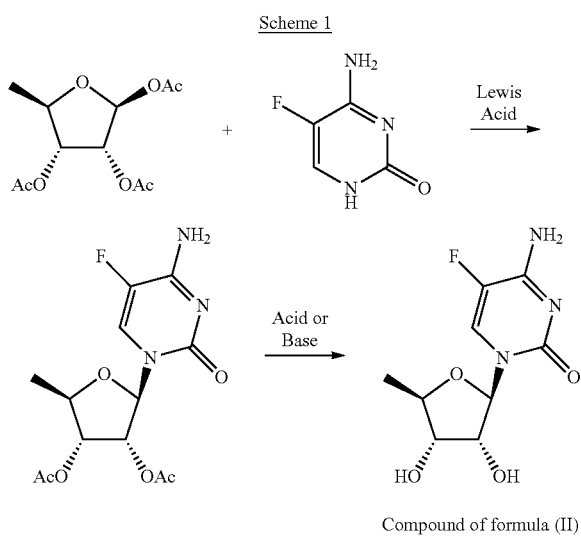

The 5 deoxy-5'-fluorocytidine compound of formula (II) is then coupled with a compound of formula (III) to afford the desired carbamate compounds. See Scheme 2 below:

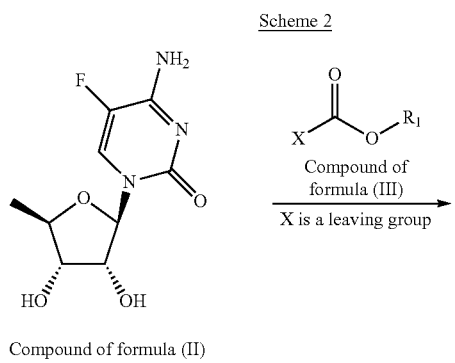

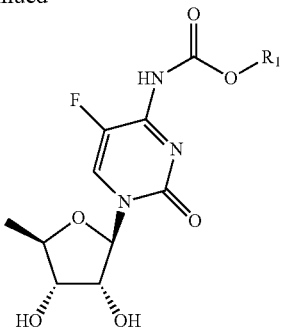

Compound of formula (I)

The moiety "X" in the compound of formula (III) is a leaving group. A leaving group can depart, upon direct displacement or ionization, with the pair of electrons from one of its covalent bonds (see, e.g., F. A. Carey and R. J. Sundberg, *Advanced Organic Chemistry*, 3$^{rd}$ Ed. Plenum Press, 1990). Examples of a leaving group include, but are not limited to, methanesulfonate, triflate ($MeSO_3^-$), p-toluenesulfonate (4-Me-Ph-$SO_3^-$), iodide, bromide, chloride, trifluoroacetate ($CF_3CO_2^-$), 4-nitrophenoxy, and N-succinimidyloxy.

The above reaction can be carried out in a solvent containing a base. The solvent can be an organic solvent or a mixture of an organic solvent and water. It preferably dissolves one or more reactants in the reaction. Examples of the solvent are acetone, acetonitrile (ACN), dimethylformamide (DMF), ethyl acetate (EA), 1,2-dichloroethane (DCE), dimethylacetamide (DMAC), dimethylsulfoxide (DMSO), tetrahydrofuran (THF), isopropyl alcohol (IPA), nitromethane, ACN/$H_2O$, or acetone/$H_2O$.

The base can be either an organic base or an inorganic base. Examples of the base include, but are not limited to, pyridine, amine (e.g., triethylamine), immidazole, 1,8-diazabicyclo[5.4.0]undec-7-ene (DBU), 1,5-diazabicyclo[4.3.0]non-5-ene (DBN), $K_2CO_3$, $Na_2CO_3$, and $NaHCO_3$.

Alternatively, the above reaction can be carried out in the presence of a catalyst. For example, a metal salt catalyst is used to promote the reaction.

One can perform the above-described reaction at room temperature or at an elevated temperature. For example, one can heat the reaction mixture to 30-100° C. or 65-85° C. or even at a temperature to reflux the solvent.

If preferred, the reaction can be performed under a protected atmosphere, e.g., nitrogen, helium, or argon.

The reaction can be monitored by a conventional method to determine whether it is complete. The commonly used method includes TLC, gas chromatography, liquid chromatograph, NMR, ultraviolent, or infrared. After the reaction is complete, one can isolate or purify desired 5-deoxy-5'-fluorocytidine compounds by conventional methods, for example, using crystallization and chromatograph. For example, the reaction mixture is first concentrated, and then charged onto a silica or alumina column to obtain the pure desired product.

Conventional chemical transformations can be used to practice this invention. One skilled person in the art would be able to determine suitable chemical agents, solvents, protecting groups, and reaction conditions for these transformations. Relevant information is described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L.

Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. For illustrative purposes, an embodiment of the process of this invention is described herein.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Synthesis of 2',3'-di-O-acetyl-5'-deoxy-5-fluorocytidine (Compound 2)

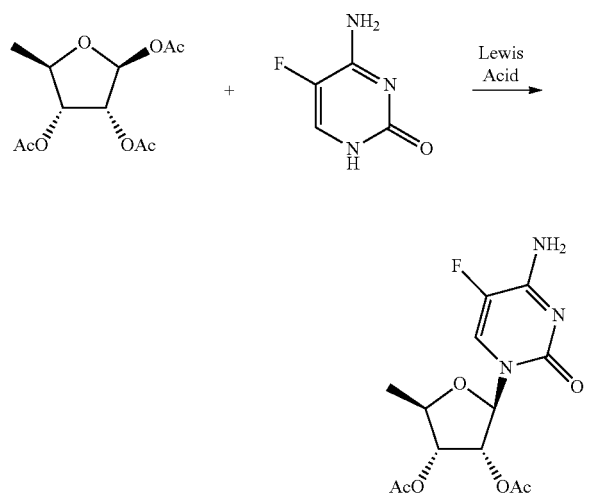

5-Fluorocytosine (5 g, 39 mmol) was suspended in toluene (20 mL), to which hexamethyl disilazane (3.6 g, 39 mmol) was then added. The mixture was heated at 105° C. for 2 hours. After the reaction mixture was concentrated under reduced pressure, methylene chloride (80 mL) and 5-deoxy-1,2,3-tri-O-acetyl-β-D-ribofuranoside (11.1 g, 43 mmol) were added, followed by addition of anhydrous stannic chloride (13.1 g, 50 mmol) dropwise at 0-10° C. over a period of 30 min. After 3 hours at room temperature, the reaction mixture was treated with sodium bicarbonate (15 g) and then water (8 mL) was added dropwise over a period of 45 min. Finally, the mixture was stirred at room temperature for 2 hours, and the precipitate was then removed by filtration and the filtrate was washed with 4% sodium bicarbonate solution (40 mL). The resultant solution was subjected to evaporation under reduced pressure, and the residue was crystallized from isopropanol (40 mL) to obtain crude compound 2 (yield: 8.7 g). mp 190±192° C.; MASS: m/z 352.11 [m+Na⁺]; $^1$H NMR (DMSO-d6): δ 1.34 (3H, d), 2.04 (3H, s), 2.05 (3H, s), 4.04 (1H, dq), 5.09 (1H, t), 5.43 (1H, dd), 5.76 (1H, d), 7.67 (1H, br s), 7.94 (1H, br s), 8.01 (1H, d).

EXAMPLE 2

Synthesis of 5'-deoxy-5-fluorocytidine (Compound 3)

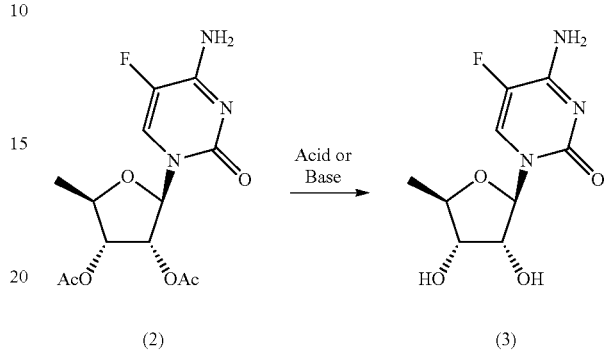

Compound 2 (5 g, 15 mmol), methanol (15 mL), and diethylamine (0.15 mL) were charged into a 50 ml round-bottom flask. The reaction mixture was heated at 55° C. for 2 hrs. Toluene (60 was then added to the mixture at 55° C.-60° C. A white solid precipitate was formed. After cooling to room temperature, the precipitate was collected by filtration to obtain crude compound 3 (yield: 3.12 g). MASS: m/z 267.94 [m+Na⁺]; 1H NMR (DMSO-d6): δ 1.26 (3H, d), 3.64-3.51 (1H, m), 3.78-3.84 (1H, m), 3.97-3.98 (1H, m), 5.03 (1H, br d), 5.28 (1H, br d), 5.67 (1H, d), 7.58 (1H, br s), 7.73 (1H, d), 7.76 (1H, br s).

EXAMPLE 3

Synthesis of 2,5-dioxopyrrolidin-1-yl pentyl carbonate (Compound 4)

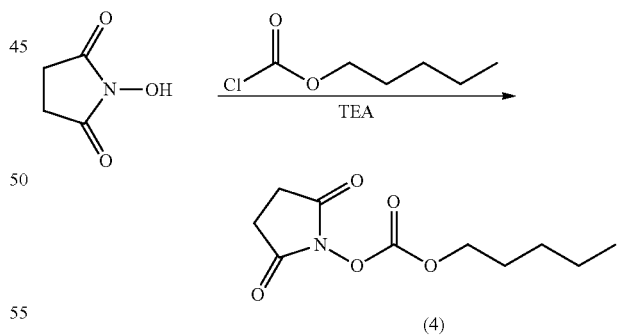

n-Hydroxysuccinimide (10 g, 86.9 mmol), triethylamine (8.8 g, 86.9 mmol) and dichloromethane (80 mL) were charged into a clean round-bottom flask. The flask was placed in ice bath. While stirring, n-pentyl chloroformate (13 g, 86.9 mmol) was added dropwise over a period of 60 min (the addition of n-pentyl chloroformate should be slow enough that the reaction temperature was kept between 0-5° C.). After the reaction mixture was stirred for an additional 10 min, it was warmed up to room temperature by stirring for 1 hr. The mixture was then poured into water (80 mL). The aqueous layer was extracted using dichloromethane, and the organic layer was dried over anhydrous $Na_2SO_4$. The filtrate was concentrated under reduced pressure to obtain Compound 4 as a clear liquid (yield: 19.5 g). GC-MASS: m/z 230.1 [m$^+$+H]; $^1$H NMR (CDCl$_3$): δ 0.94 (3H, t), 1.35-1.39 (4H, m), 1.65-1.80 (2H, m), 2.84 (4H, s), 4.32 (2H, t).

EXAMPLE 4

Synthesis of Capecitabine (Compound 1) from Compounds 3 and 4

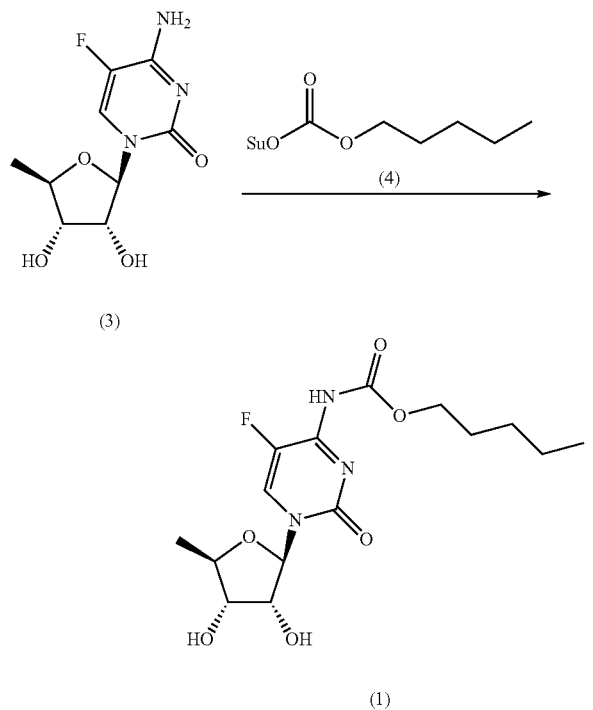

Compound 3 (5 g, 20 mmol), Compound 4 (9.3 g, 40 mmol) and dimethylformamide (25 mL) were charged into a clean round-bottom flask. The reaction mixture was heated up to 65° C. and stirred for 20 hrs. Upon completion of the reaction, the organic solvent was removed by distillation at 50° C. The mixture was then poured into dichloromethane (50 mL), and the solution was cooled to 0-5° C. 5 N NaOH (25 mL) was added dropwise into the solution at 0-5° C. over a period of 30 min. The resulting mixture was stirred for an additional 20 min. The mixture was then placed in the ice bath. While the mixture was stirring, it was treated with concentrated HCl drop by drop over a period of 25 min, with the temperature being kept at 0-5° C. Then pH of the reaction mixture was adjusted from 14 to 5. The aqueous layer was extracted with dichloromethane (50 mL×3), and the organic layer was dried over anhydrous $Na_2SO_4$ and filtered. The filtrate was concentrated under reduced pressure to give an oily residue, which was dissolved in EA (15 mL). While stirring, n-hexane (30 mL) was added dropwise over a period of 20 min to this solution. The resulting solution was allowed to stand at room temperature for 4 h. The white solid precipitate was collected by filtration and washed with n-hexane to obtain Compound 1 (yield: 3.15 g). mp 117±119° C.; MASS: m/z 382.05 [m+Na$^+$]; 1H NMR (DMSO-d6): δ0.88 (3H, t), 1.29-1.33 (4H, m), 1.31 (3H, d), 1.60 (2H, m), 3.66 (1H, q), 3.89 (1H, m), 4.04-4.09 (3H, m), 5.05 (1H, d), 5.41 (1H, d), 5.66 (1H, d), 7.98 (1H, br s).

EXAMPLE 5

Synthesis of Compound 1 from Compound 3 and n-pentyl chloroformate

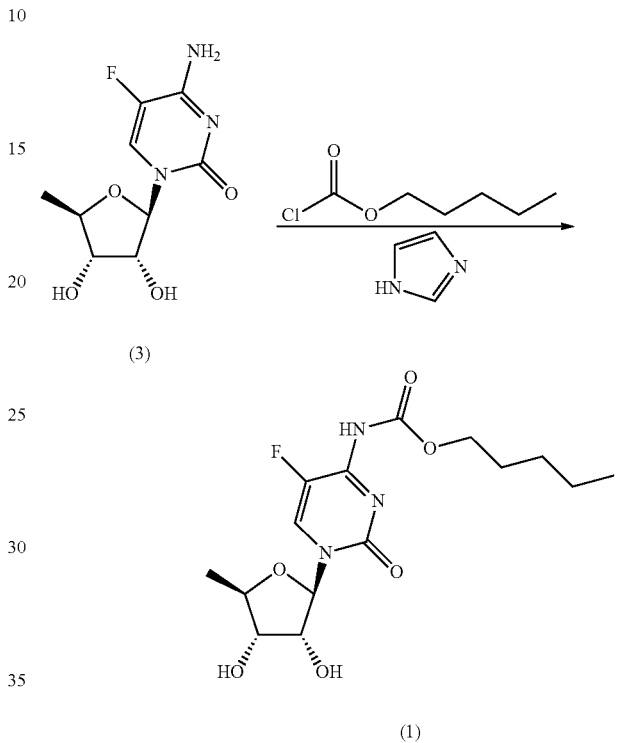

Compound 3 (1 g, 4 mmol), imidazole (0.64 g, 9.2 mmol), and dimethylformamide (5 mL) were charged into a clean round-bottom flask. The flask was placed in an ice bath. While stirring, n-pentyl chloroformate (1.2 g, 8 mmol) was added dropwise slowly over a period of 90 min so that the reaction temperature was kept between 0-5° C. The reaction mixture was heated to 45° C. after an addition 10-min stirring, and was stirred for another 16 hrs. Upon completion of the reaction, the organic solvent was removed by distillation at 50° C. The residue mixture was poured into dichloromethane (10 mL), and the solution was cooled to 0-5° C. 4 N NaOH (5 nit) was added dropwise into the solution at 0-5° C.; over a period of 30 min, followed by an addition 20 min stirring. The mixture was placed in an ice bath, and concentrated HCl was added dropwise over a period of 25 min while the mixture was stirred and kept at 0-5° C. Then pH of the mixture was adjusted from 14 to 5. The aqueous layer was extracted with dichloromethane (10 mL×3), and the organic layer was dried over anhydrous $Na_2SO_4$ and filtered. The filtrate was concentrated under reduced pressure to give an oily residue, which was dissolved in dichloromethane (2 mL). Toluene (20 mL) was added dropwise to the solution over a period of 15 min while stirring, and the resulting solution was allowed to stand at room temperature for 16 hrs. The white solid precipitate was collected by filtration and washed with toluene to obtain Compound 1 (yield: 0.68 g). See Example 5 above for mp, MASS, and NMR data.

EXAMPLE 6

Synthesis of Compound 1 from Compound 3 and 4-nitrophenyl pentyl carbonate (Compound 5)

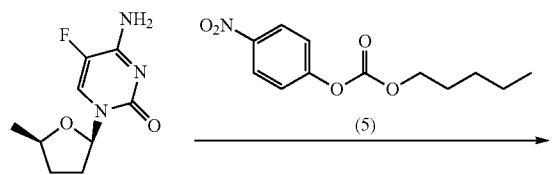

(3)

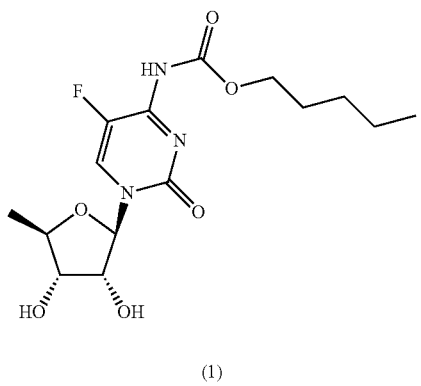

(1)

Compound 3 (1 g, 4 mmol), Compound 5 (2 g, 8 mmol), and dimethylformamide (5 mL) were charged into a clean round-bottom flask. The reaction mixture was heated to 65° C. and stirred for 20 hrs. Upon completion of the reaction, the organic solvent was removed by distillation at 50° C. to obtain Compound 1 (yield: 1.85 g). See Example 5 above for mp, MASS, and NMR data.

The tables below show yields of the reaction under various reaction conditions:

TABLE 1

| Entry | Base (eq) | X (eq) | Temp | Solvent | DHC (AP) | CPTB (AP) | Bis (AP) |
|---|---|---|---|---|---|---|---|
| 1 | Pyridine (1) | Cl (1) | 5° C. | DCM | 17.62 | 38.18 | 19.26 |
| 2 | Pyridine (1) | Cl (1) | 25° C. | DCM | 17.31 | 43.61 | 17.55 |
| 3 | Pyridine (2) | Cl (2) | 5° C. | DCM | 0 | 31.1 | 36.06 |
| 4 | Pyridine (1) | Cl (1) | 5° C. | DMF | 19.17 | 56.54 | 10.02 |
| 5 | NEt3 (1) | Cl (1) | 5° C. | DCM | 28.36 | 2.56 | 11.56 |
| 6 | Imidazole(2.3) | Cl (2) | 40° C. | DMF | 3.54 | 65.4 | 22.8 |
| 7 | Imidazole(2.3) | Cl (2) | 40° C. | DCM | 85 | 15 | 0 |
| 8 | Pyridine (1) | OSu (1) | 5° C. | DCM | 79.91 | 4.51 | 0 |
| 9 | K2CO3 (1) | OSu (1) | 5° C. | ACN | 82.89 | 5.44 | 0 |
| 10 | Pyridine (1) | OSu(1) | 5° C. | DMF | 94.37 | 1.89 | 0 |
| 11 | Pyridine (1) | OSu (1) | 65° C. | DMF | 41.23 | 56.77 | 0 |

TABLE 2

| Entry | X (eq) | Temp | Solvent | Time (h) | DHC (%) | CPTB (%) | Note |
|---|---|---|---|---|---|---|---|
| 1 | OSu (2) | 80° C. | DMF | 20 | 26.1 | 62.7 | |
| 2 | Osu (2) | 65° C. | DMF | 20 | 24.3 | 67.6 | |
| 3 | Osu (2) | 65° C. | DMF | 20 | 18.4 | 64.0 | Add NHS (1) at first |
| 4 | Cl (1) | 65° C. | DMF | 16 | 75 | 0 | Add Cl (1) dropwise |
| 5 | NP(1) | 65° C. | DMF | 20 | 65 | 21 | |
| 6 | NP(1.5) | 65° C. | DMF | 20 | 29.11 | 33.76 | |
| 7 | NP(3) | 65° C. | DMF | 20 | 3.53 | 28.1 | |

TABLE 3

| No | X (eq) | Temp | Solvent | Time | DHC (%) | CPTB(%) | RC C (%) | Note |
|---|---|---|---|---|---|---|---|---|
| 1 | OSu (2) | 65° C. | DMF | 20 h | 15 | 73 | 5 | |
| 2 | OSu (2) | 65° C. | DMSO | 20 h | 11 | 71 | 8 | |
| 3 | OSu (2) | 65° C. | ACN | 20 h | 21 | 70 | | |
| 4 | OSu (2) | 65° C. | EA | 16 h | 31 | 58 | | |
| 5 | OSu (2) | 65° C. | IPA | 16 h | 25 | 58 | 0.16 | 9% Impurity |
| 6 | OSu (2) | 65° C. | Nittromethane | 16 h | 34 | 51 | 6 | |
| 7 | OSu (2) | 65° C. | Acetone + 5%H2O | 16 h | 24 | 65 | | |
| 8 | OSu (2) | 65° C. | H2O | 16 h | 97 | 0.3 | | |
| 9 | OSu (2) | 65° C. | ACN + 5%H2O | 16 h | 18 | 68 | | |
| 10 | OSu (2) | 65° C. | DMAC | 16 h | 15 | 70 | 4 | |
| 11 | OSu (2) | 65° C. | DCM:H2O(5:1) | 16 h | 23 | 59 | 3 | |
| 12 | OSu (2) | 65° C. | THF | 16 h | 22 | 54 | 6 | |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent of similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A process of preparing a β-nucleoside compound of formula (I):

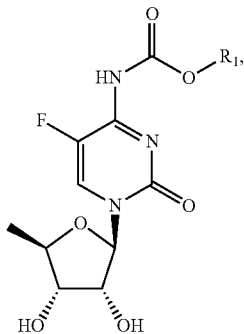

wherein R₁ is alkyl, alkenyl, aryl, cycloalkyl, heteroaryl, or heterocycloalkyl, said process comprising hydrolyzing a bi-OH-protected compound of Formula (II) in the presence of an acid or base to obtain a compound of formula (II), and reacting the compound of formula (II) thus obtained:

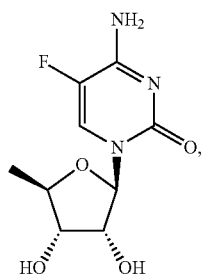

with a compound of formula (III):

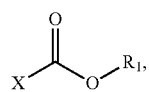

wherein R₁ is as defined above and X is chloride, bromide, iodide, methanesulfonate, triflate, p-toluenesulfonate, trifluoroacetate, 4-nitrophenoxy, or N-succinimidyloxy, in a solvent and in the presence of a base.

2. The process of claim 1, wherein the base is selected from the group consisting of pyridine, imidazole, ammonia, a monoalkylamine, a dialkylamine, a trialkylamine, sodium carbonate, and potassium carbonate.

3. The process of claim 1, wherein the solvent is acetone, acetonitrile (ACN), dimethylformamide (DMF), ethyl acetate (EA), 1,2-dichloroethane (DCE), dimethylacetamide (DMAC), dimethylsulfoxide (DMSO), tetrahydrofuran (THF), isopropyl alcohol (IPA), or nitromethane, or a mixture of ACN/H₂O or acetone/H₂O.

4. The process of claim 1, wherein X is Cl, 4-nitrophenoxy, or N-succinimidyloxy.

5. The process of claim 1, wherein R₁ is alkyl.

6. The process of claim 5, wherein R₁ is n-pentyl.

7. The process of claim 1, wherein the base is pyridine or imidazole.

8. The process of claim 6, wherein X is Cl, 4-nitrophenoxy, or N-succinimidyloxy.

9. The process of claim 8, wherein the base is pyridine or imidazole.

10. The process of claim 9, wherein the solvent is acetone, acetonitrile (ACN), dimethylformamide (DMF), ethyl acetate (EA), 1,2-dichloroethane (DCE), dimethylacetamide (DMAC), dimethylsulfoxide (DMSO), tetrahydrofuran (THF), isopropyl alcohol (IPA), or nitromethane, or a mixture of ACN/H₂O or acetone/H₂O.

11. The process of claim 10, wherein the solvent is DMF, DMSO, or DMAC.

12. The process of claim 11, wherein X is Cl.

13. The process of claim 12, where the base is pyridine.

14. The process of claim 13, wherein the reaction is carried out at a temperature of 50-100° C.

15. The process of claim 14, wherein the reaction is carried out at a temperature of 65-80° C.

16. The process of claim 1, wherein the reaction is carried out at a temperature of 50-100° C.

17. The process of claim 16, wherein the reaction is carried out at a temperature of 65-80° C.

* * * * *